United States Patent [19]

Jinno et al.

[11] Patent Number: 4,744,654
[45] Date of Patent: May 17, 1988

[54] METHOD OF MEASURING REFRACTIVE INDEX PROFILE OF CYLINDER

[75] Inventors: Hiroshi Jinno, Kyoto; Takeshi Yao, Hirakata, both of Japan

[73] Assignee: Kyoto University, Kyoto, Japan

[21] Appl. No.: 63,810

[22] Filed: Jun. 17, 1987

Related U.S. Application Data

[63] Continuation-in-part of Ser. No. 715,298, Mar. 25, 1985, abandoned.

[30] Foreign Application Priority Data

Sep. 14, 1984 [JP] Japan .................. 59-191645

[51] Int. Cl.$^4$ .................................. G01N 21/41
[52] U.S. Cl. ................... 356/73.1; 356/128
[58] Field of Search ................... 356/128, 73.1

[56] References Cited

U.S. PATENT DOCUMENTS

| | | | |
|---|---|---|---|
| 4,227,806 | 10/1980 | Watkins | 356/73.1 |
| 4,422,733 | 12/1983 | Kikuchi et al. | 350/413 |
| 4,441,811 | 4/1984 | Melezoglu et al. | 356/73.1 |
| 4,492,463 | 1/1985 | Marcuse et al. | 356/73.1 |

OTHER PUBLICATIONS

Watkins "Laser Beam Refraction Traversely Through a Graded-Index Preform to Determine Refractive Index Ratio and Gradient Profile" *Applied Optics*, vol. 18. No. 13 (Jul. 1, 1979) pp. 2214–2222.

P101 Preform Analyser by York Technology.

"Nondestructive Measurement of Index Profile of an Optical-Fibre Preform" by P. L. Chu, Electronics Letters, vol. 13, No. 24, 736–738 (1977).

"Measurement of Refractivce-Index Profile of Optical Fibre Preform", by P. L. Chu & T. Whitebread, Electronics Letters, vol. 15, No. 10, pp. 295–296 (1979).

"Measurement of Refractice-Index Profiles in Optical-Fibre Preforms by Spatial-Filtering Technique", by I. Sasaki, D. N. Payne, & M. J. Adams, Electronics Letters, vol. 16, No. 6 (1980).

*Primary Examiner*—R. A. Rosenberger
*Attorney, Agent, or Firm*—Fleit, Jacobson, Cohn & Price

[57] ABSTRACT

Parallel light rays are applied to a cylinder and true exit positions of the rays from the cylinder are measured, phantom exit positions for the incident rays are calculated by using a mathematical function representing a phantom refractive index profile, and the mathematical function is modified so as to minimize the sum of the squared differences between the true and phantom exit positions.

5 Claims, 6 Drawing Sheets

FIG_1

FIG_2

FIG_3

FIG_3A

FIG_3B

FIG_3C

FIG_6

FIG_7

FIG_8

METHOD OF MEASURING REFRACTIVE INDEX PROFILE OF CYLINDER

This application is a continuation-in-part of application Ser. No. 715,298 filed Mar. 25, 1985, now abandoned.

BACKGROUND OF THE INVENTION

1. Field of the Invention

This invention relates to a method of measuring refractive index profile of a cylinder having a circular cross section with distributed refractive index, such as optical fibers and lenses. The method of the invention has a high resolution and it is particularly useful for accurately determining the refractive index profile of a cylinder having a large difference of refractive index between the central and peripheral portions thereof.

2. Description of the Prior Art

In general, a cylindrical optical element (to be referred to as "cylinder", hereinafter) having a circular cross section with distributed refractive index, such as optical fibers and lenses with distributed refractive index, has a very wide range of application in optical technology and it is highly useful. With such cylinders, the distribution pattern of their internal refractive index exerts critical influence on the optical characteristics and performance of the cylinders. Accordingly, various methods for measuring the refractive index profile of the cylinder have been developed heretofore. Typical non-destructive methods of measuring the refractive index profile of the cylinder by using incident rays perpendicular to its longitudinal axis will be briefly reviewed.

Figure 6:
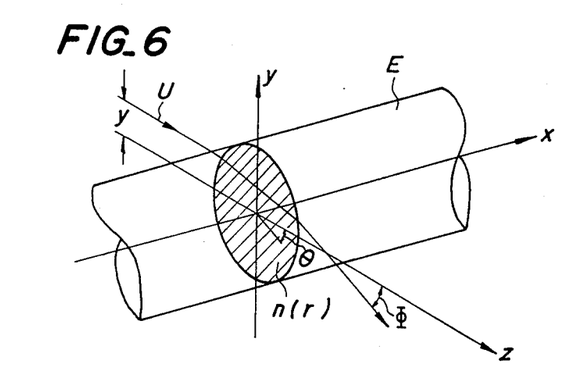
FIG. 6 is a schematic perspective view of a cylinder being measured, showing the deflection angle Φ of a ray of light leaving the cylinder, which deflection angle is used in various methods of the prior art.

Referring to FIG. 6, a three-dimensional orthogonal coordinate system is considered with the x-axis aligned with the longitudinal axis of a cylinder E. When a ray of light (to be referred to as the ray) U is applied to the cylinder E at right angles to the longitudinal axis, i.e., in parallel to the z-axis, with a distance y to the z-axis, the ray U proceeds through the cylinder E along a curved optical path depending on the distribution of refractive index in the cylinder, so that the ray U leaves the cylinder E with a deflection angle $\Phi$ relative to the z-axis. Thus, the magnitude of the deflection angle $\Phi$ reflects the refractive index distribution in the cylinder E. The deflection angle $\Phi$ is expressed as a function of the spacing y of the incident ray U from the z-axis, namely a deflection function $\Phi(y)$. The spacing y is indicative of the incident position of the ray U into the cylinder E.

A number of methods have been proposed to measure the refractive index profile of the cylinder E from the deflection function $\Phi(y)$. Those methods facilitate the non-destructive measurement but have a shortcoming in that the deflection angle can be measured only when the cylinder is placed in a medium whose refractive index is the same as that at the periphery of the cylinder. To this end, the cylinder must be immersed in an index-matching fluid having the same refractive index as that of the cylinder periphery. Besides, the equation representing the optical path in the cylinder, which is necessary for the determination of the refractive index profile of the cylinder based on the reflection function $\Phi(y)$, has been solved only for the case of the cylinder surrounded by the index-matching fluid.

The conventional methods of measuring the refractive index profile have been used only with preforms which are interim products for making optical fibers. In the preforms and optical fibers, the difference of the refractive index between the core portion and the peripheral portion thereof is small. Thus, the conventional methods have not been intended to measure the refractive index in lenses of distributed refractive index type, in which the refractive index difference between the core portion and the peripheral portion is large.

Four practical methods have been known for determining the refractive index profile of a cylinder by measuring the deflection function $\Phi(y)$.

(a) Laser beam scanning method

A sharply defined laser beam is directed to a cylinder so that the beam becomes incident to the cylinder at right angles to the longitudinal axis thereof. The direction in which the thus directed laser beam leaves the cylinder is measured, so as to directly determine the deflection angle $\Phi$. The spacing y of the focussed laser beam from the z-axis (see FIG. 6) is changed in steps and the deflection angle is determined for each step of the spacing y, so as to derive the deflection function $\Phi(y)$ from which the refractive index profile of the cylinder can be calculated. The principle of this method is very simple, but it is difficult to accurately measure the deflection angle $\Phi$.

Examples of published methods for obtaining the deflection angle $\Phi$ are the P101 Preform Analyser by York Technology; "Nondestructive Measurement of Index Profile of an Optical-Fibre Preform" by P. L. Chu, Electronics Letters, Vol. 13, No. 24, pp. 736-738 (1977); "Measurement of Refractice-Index Profile of Optical Fibre Preform", by P. L. Chu and T. Whitebread, Electronics Letters, Vol. 15, No. 10, pp. 295-296 (1979); "Measurement of Refractice-Index Profiles in Optical-Fibre Preforms by Spatial-Filtering Technique", by I. Sasaki, D. N. Payne, and M. J. Adams, Electronics Letters, Vol. 16, No. 6 (1980); and "Laser Beam Refraction Traversely Through a Graded-Index Preform to Determine Refractive Index Ratio and Gradient Profile", by L. S. Watkins, Applied Optics, Vol. 18, No. 13 (1979).

(b) Focussing method

Parallel rays are uniformly directed to a cylinder so that the rays become incident to the cylinder at right angles to the longitudinal axis thereof. The deflection function $\Phi(y)$ is determined from the intensity distribution of the thus directed rays after they leave the cylinder, and the refractive index profile of the cylinder is calculated from the deflection function. As compared with the direct measurement of the deflection angle $\Phi$ of the preceding method, the measurement of the intensity distribution or intensity change of the rays in this method is easier. However, this method involves an assumption that the incident rays are parallel and never cross with each other, which assumption cannot be realized in practice. Accordingly, this method has a shortcoming in that its spatial resolution is limited.

(c) Spatial filtering method I

Figure 7:
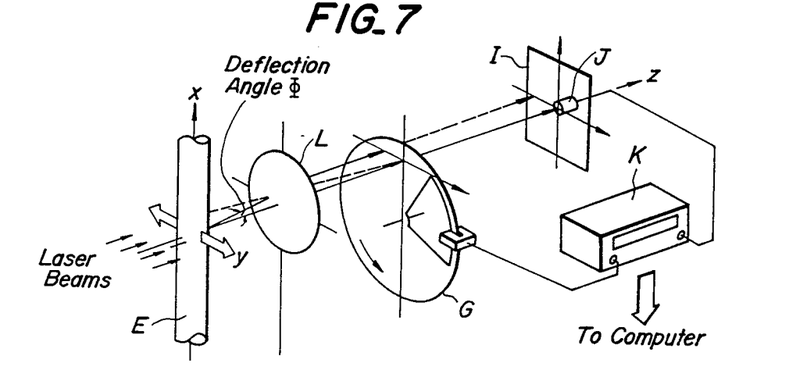
FIG. 7 is a schematic perspective view of an optical system of a conventional spatial filtering method of measuring refractive index profile of a cylinder.

Referring to FIG. 7, when one of distinct parallel laser beams on a plane perpendicular to the longitudinal axis of a cylinder E such as a preform of optical fibers or the x-axis of FIG. 7 becomes incident to the cylinder E immersed in an index-matching fluid, the beam suffers from deflection while passing through the cylinder E. The deflected beam from the cylinder E is bent by a focussing lens L, so that the beam passes through a focal plane of the lens L at a point which is spaced from the focal point of the lens L by a distance depending on the deflection caused by the cylinder E. Then, the beam is projected onto an image screen I. An optical rotary chopper G or a spatial filter is turned on the above-mentioned focal plane at a constant speed, so that the beam from the lens L is intermittently interrupted by the optical chopper G. The duration of the beam passage through the chopper G depends on the magnitude of the beam deviation from the focal point on the focal plane.

A light detector J disposed on the image screen I generates ON-OFF signals depending on the presence and absence of the beam projected on the image screen I. The ON portion of the ON-OFF signal represents the duration of the beam passage through the light chopper G, and a time-interval-measuring counter K receives such ON-OFF signals and measures the duration of such beam passage. The thus measured duration of the beam passage indicates the deflection angle $\Phi$ caused by the cylinder E.

The deflection function $\Phi(y)$ can be determined by shifting the cylinder E in steps in a direction perpendicular to the incident laser beams or in the y-axis direction of FIG. 7 and measuring the deflection angle $\Phi$ for each step of the shift. The refractive index profile of the cylinder E can be determined from the deflection function $\Phi(y)$ as described above.

(d) Spatial filtering method II

Figure 8:
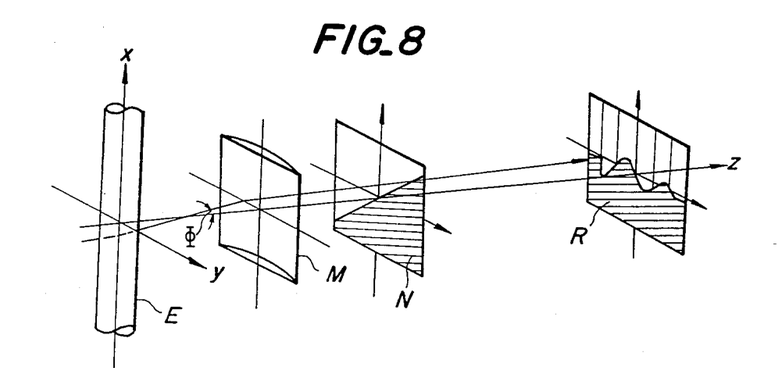
FIG. 8 is a schematic perspective view of an optical system of a modified spatial filtering method of the prior art.

Referring to FIG. 8, uniform parallel rays of light on a plane perpendicular to the longitudinal axis of a cylinder E or the x-axis are applied to the cylinder E, and the rays suffer from deflection while passing through the cylinder E. The deflected rays are bent by a cylindrical lens M and filtered by a spatial filter N disposed on the focal plane of the cylindrical lens M, so as to produce an image R of the spatial filter N whose configuration indicates the deflection suffered by the incident light rays while passing through the cylinder E. A deflection function $\Phi(y)$ is determined from the configuration of the image R, and the refractive index profile of the cylinder E is derived from the deflection function $\Phi(y)$.

The above conventional methods for measuring the refractive index profile of a cylinder facilitates the non-destructive measurement. However, each of such conventional methods has a shortcoming in that it requires the immersion of the cylinder E in an index-matching fluid, so that the measurement by the conventional methods is restricted to immersible cylinders and the process of measurement has been complicated and cumbersome. The index-matching fluid has been necessary because the conventional methods measure the deflection angle, which measurement has been possible only when the refractive index of the medium surrounding the cylinder E is the same as that of the cylinder periphery, namely only when the cylinder is immersed in an index-matching fluid. Besides, the equation giving the optical path in the cylinder, which is essential in deriving the refractive index profile of the cylinder from its deflection function $\Phi(y)$, has been solved only in the case that the medium surrounding the cylinder is an index-matching fluid or the like which has the same refractive index as that of the cylinder.

Actual use of the conventional methods has been limited to the measurement of the refractive index of preforms from which optical fibers are produced. In typical preforms, the differences of the refractive index between the core portion and the peripheral portion is small. Thus, the conventional methods have another shortcoming in that no attention has been paid to the measurement of a lens of distributed refractive index type with a wide difference of refractive index therein.

In the case of optical fiber, its signal transmission characteristics is considerably affected by a deviation of the refractive index profile of a preform from which it is drawn, and such deviation may be caused by a minor control error during the production of the preform. The refractive index profile pattern of the preform having a large diameter is maintained substantially intact in the optical fiber having a small diameter drawn from the preform. Accordingly, the yield of the optical fiber production can be improved by precise quality control in the stage of preform production through feedback control based on the result of refractive index profile measurement. If the refractive index profile of the preform is measured in a non-destructive manner before the drawing so as to select those which have good refractive index distribution pattern, the yield of the optical fiber production will be further improved by drawing it only from the thus selected good preforms.

In the production of a lens with distributed refractive index, the measurement of the refractive index profile is also important. Such lens is produced by any of various methods; such as the ion-exchange method, the ion implantation method, the neutron erradiation method, the high polymer diffusion-polymerization method, and the molecular stuffing method.

In the ion-exchange method, an interim-product lens which contains ions with high electron polarizability, such as thallium ions ($Tl^+$), cesium ions ($Cs^+$), or silver ions ($Ag^+$) is brought in contact with a molten salt at a high temperature. Whereby, such ions are diffused from the lens so as to produce an ionic concentration distribution, whereby a refractive index profile is formed. A number of semi-empirical techniques are combined in the above diffusion process, and no theoretical analysis of the process has been completed yet. On the other hand, precise control of the diffusion process is indispensable because the pattern of refractive index profile critically affects the performance of the lens. If feedback control is applied to the diffusion process for producing the refractive index profile pattern by using the result of non-destructive measurement of the refractive index distribution, the desired pattern of the refractive index distribution can be accurately produced.

The non-destructive measurement of the refractive index profile of the lens thus produced will facilitate selection of those having excellent refractive index distribution pattern. Accordingly, the quality control of the finished lens will be greatly simplified by such non-destructive measurement.

Much time and labor are necessary to produce the index-matching fluid, to which the cylinder being measured must be immersed in the above-mentioned conventional methods of measurement. The immersion of the cylinder in the index-matching fluid makes it very difficult to use the conventional measuring method in the midst of production process involving treatments of the cylinder in different environments, so that the conventional measuring methods is not suitable for the feedback control of the production process by any means.

SUMMARY OF THE INVENTION

Therefore, an object of the invention is to obviate the above-mentioned shortcomings of the prior art by providing an improved method of measuring the refractive index profile of a cylinder. The measuring method of the invention is effective even when a cylinder has a large refractive index difference between the central and peripheral portions thereof. Besides, the method of the invention ensures excellent result of measurement regardless of environments in which the cylinder being measured is placed.

Another object of the invention is to provide a method of measuring the refractive index profile of a cylinder, which method is suitable for producing measured values applicable to precise feedback control of the process of manufacturing cylinders having a desired pattern of refractive index profile.

A further object of the invention is to provide a method of measuring the refractive index profile of a cylinder, which method does not require any index-matching fluid surrounding the cylinder being measured.

It is another object of the invention to provide a method of measuring the refractive index profile of a cylinder, which method facilitates the quality control of finished cylinder products.

Another object of the invention is to provide a method of measuring the refractive index profile of a cylindrical lens of distributed refractive index type with a large difference of refractive index therein, such as a glass cylinder having a substantially parabolic distribution of refractive index along the radial direction thereof. The cylindrical lens of the distributed refractive index type is used as a convex-lens-like optical element in optical communications system, copying machines, optical disks and various other technical fields; for instance, as an optical coupler, an optical branch device, an optical connector, an optical attenuator, an optical switch, etc.

In a preferred embodiment of the method of measuring refractive index profile of a cylinder according to the invention, k distinct parallel rays are formed on one plane perpendicular to longitudinal axis of said cylinder, and the parallel rays are applied to the cylinder so that the rays enter the cylinder at incident positions $P_1, P_2, \ldots, P_k$ and leave the cylinder at true exit positions $Q_1, Q_2, \ldots, Q_k$. The incident positions and the true exit positions are determined by measurement. A mathematical function representing a phantom refractive index profile of the cylinder on said plane is assumed, and phantom exit positions $Q_1', Q_2', \ldots, Q_k'$ for the parallel rays from said incident positions are calculated based on the thus assumed mathematical function. Then, the above function is modified so as to minimize the sum of squared distances between the true and phantom exit positions for the rays from said incident positions. Whereby, the thus modified function represents the refractive index profile of the cylinder.

The above-mentioned mathematical function may be in the form of $$F(r, a_1, a_2, \ldots, a_m),$$

r being the distance from an arbitrary point in the cylinder to the longitudinal axis of the cylinder, $a_1$ through $a_m$ being parameters representing pattern of the refractive index profile of the cylinder, the number m of the parameters being not greater the number k of the ray ($k \geq m$).

In a simplified example of the method of the invention, the above-mentioned mathematical function may be in the form of $$n(r, n_0, g) = n_0\sqrt{1-(gr)^2},$$

n being refractive index, $n_0$ being refractive index at the longitudinal axis of the cylinder, r being the distance from an arbitrary point in the cylinder to said longitudinal axis of the cylinder, and g being a focusing constant.

In the practical applications of the method of the invention, the above-mentioned plane of the parallel rays may be shifted in the longitudinal direction of the cylinder while keeping the plane perpendicular to said longitudinal axis, so as to determine a refractive index profile on the thus moved plane. Whereby the refractive index profile in the longitudinal direction of the cylinder is measured.

BRIEF DESCRIPTION OF THE DRAWINGS

For a better understanding of the invention, reference is made to the accompanying drawings, in which.

Throughout different views of the drawings, A is a light source, B is a pinhole or slit, D is a sensor, E is a cylinder, F is a mathematical function, G is an optical chopper, I is an image screen, J is a light detector, K is a time-interval-measuring counter, L is a focussing lens, M is a cylindrical lens, N is a spatial filter, $P_i$ is an incident position, $Q_i$ is a true exit position, $Q_i'$ is a phantom exit position, R is an image, S is a curve showing the assumed refractive index profile, T is a curve showing the calculated refractive index profile, U is a ray of light, W is a curve showing the difference between the curve S and T on an exaggerated scale Φ is a deflection angle.

DESCRIPTION OF THE PREFERRED EMBODIMENTS

The invention will be described in detail now while comparing it with the prior art.

Referring to FIG. 6, in the conventional methods, the refraction index profile of a cylinder E has been determined by measuring the deflection angle Φ for each ray of light U entering the cylinder at an incident position with a spacing y from the z-axis, finding out the deflection function Φ(y) by changing the magnitude of the above spacing y and measuring the deflection angle for each magnitude of the spacing y, and calculating the profile from the thus found deflection function. If the cylinder is not surrounded by a medium having the same refractive index as that of the peripheral portion of the cylinder, e.g., an index-matching fluid, the ray of light leaving the cylinder is considerably refracted at the boundary between the cylinder and the surrounding medium, so that it is very difficult to measure the deflection angle Φ. Besides, the equation representing the optical path in the cylinder, which is essential to the calculation of the refractive index profile from the deflection function Φ(y), has been solved only for the case of the cyliner immersed in the index-matching fluid.

Figure 1:
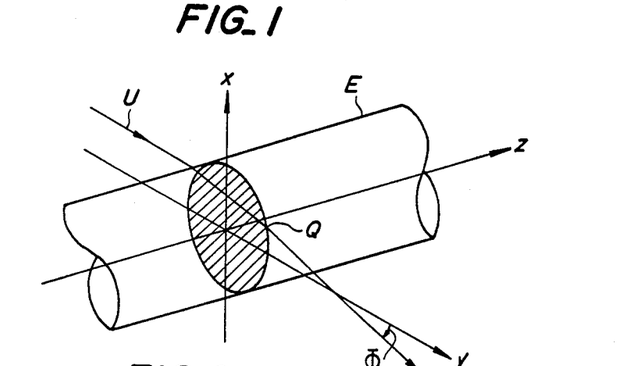
FIG. 1 is a schematic perspective view of a cylinder being measured, showing the exit position Q of a ray of light from the cylinder, which exit position is critical in the method according to the present invention.

On the other hand, in the method according to the present invention, what is actually measured is not the deflection angle Φ but the true exit position Q where the ray U leaves the cylinder E as shown in FIG. 1. The ray U becomes incident to the cylinder E at right angles to the longitudinal axis or the z-axis of the cylinder E. The refractive index profile of the cylinder E is determined from the exit position Q thus measured. More particularly, with the method according to the invention, the exit position Q is used to determine the refractive index profile, so that refractive index profile measurement by the method of the invention is not affected at all by the refraction on the outer surface of the cylinder being measured. Thus, in the method of the invention, the cylinder being measured need not be surrounded by any index-matching fluid.

Further, the inventors have derived equations which express the optical path in the cylinder by using the incident position regardless of the refractive index of its environment, so as to facilitate the determination of the refractive index profile from the exit positions. The derivation of the equations did not include any approximation. Accordingly, with the method of the invention, the refractive index profile of a cylinder can be determined without being affected by the refractive index difference between the inside and the outside of the cylinder, and such refractive index profile can be determined even if a cylinder has a large difference of refractive index between the core portion and the peripheral portion thereof.

It is an important feature that the method according to the invention can be practised by slightly modifying the above-mentioned conventional techniques, namely by measuring the true exit positions Q instead of the deflection angle Φ. Especially, the techniques and devices of the above-mentioned laser beam scanning method and the spatial filtering methods can be used in carrying out the method of the invention.

The operating principles of the method of measuring the refractive index profile of a cylinder according to the invention will be described now.

Figure 2:
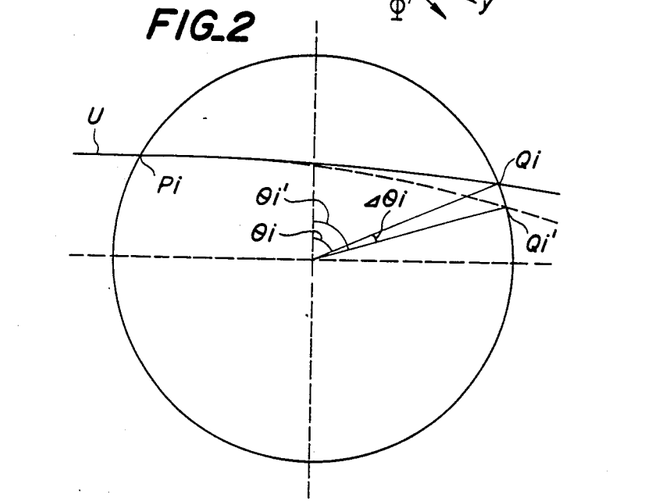
FIG. 2 is a diagrammatic illustration of the operating principle of the method according to the invention.

Referring to FIG. 2 showing a cross-section of a cylinder, a ray of light U enters into the cylinder at an incident position $P_i$ at right angles to the longitudinal axis of the cylinder, suffers from deflection while travelling through the cylinder, and leaves the cylinder at a true exit position $Q_i$. In the figure, those deflections of the optical path at the incident position $P_i$ and the true exit position $Q_i$ which are due to the difference of refractive index between the cylinder and the surrounding medium are not shown, because the method of the invention is not affected by such deflections due to the refractive index difference at the boundary positions $P_i$ and $Q_i$. The method of the invention uses k rays of light entering the cylinder at incident positions $P_1$, $P_2$, ..., $P_k$. The true exit positions $Q_1$, $Q_2$, ..., $Q_k$ where such rays leave the cylinder are measured, and the refractive index profile of the cylinder is determined from the relationship between such incident positions and the true exit positions in the following manner.

(1) It is assumed that a phantom profile of refractive index for a cylinder being measured is represented by a mathematical function $F(r, a_1, a_2, ..., a_m)$, wherein r represents the distance from the longitudinal axis of the cylinder to an arbitrary point in the cylinder and $a_1$ through $a_m$ are parameters defining the pattern of the refractive index profile. The number m of the parameters is not larger than the number k of the incident rays of light, i.e., $k \geq m$. Sometimes, r may be referred to as a radius.

(2) Phantom exit positions $Q_1'$, $Q_2'$, ..., $Q_k'$ for the above-mentioned rays entering the cylinder at the incident positions $P_1$, $P_2$, ..., $P_k$ are calculated by assuming phantom optical paths corresponding to the phantom reflective index profile as shown by the dash line curve of FIG. 2. In this calculation, the phantom refractive index profile expressed by the above mathematical function $F(r, a_1, a_2, ... a_m)$ is assumed. If the function assumed in the above calculation of the optical path, i.e., $F(r, a_1, a_2, ..., a_m)$, should represent the true refractive index profile of the cylinder, the calculated phantom exit positions $Q_1'$, $Q_2'$, ..., $Q_k'$ would coincide with the above true exit positions $Q_1$, $Q_2$, ..., $Q_k$.

On the other hand, if the assumed function $F(r, a_1, a_2, ... a_m)$ is different from a function representing the true refractive index profile of the cylinder, the calculated phantom exit positions $Q_1'$, $Q_2'$, ..., $Q_k'$ will be different from the above true exit positions $Q_1$, $Q_2$, ..., $Q_k$.

(3) When the calculated phantom exit positions Q' differ froam the measured true exit positions Q, the parameters $a_1$ through $a_m$ of the assumed function F are modified in such a manner that the sum of the squared differences between the true exit positions Q and the phantom exit positions Q' is minimized, and the phantom exit positions Q' is recalculated. Such modification and recalculation are repeated.

More particularly, when the polar coordinates of the true exit position Q and the phantom exit position Q' are denoted by $(r, \theta)$ and $(r, \theta')$, the modification of the parameters $a_1$ through $a_m$ is effected so as to minimize the following difference Δ.

$$\Delta = \sum_{i=1}^{m} (\theta_i - \theta_i')^2 = \sum_{i=1}^{m} (\Delta\theta_i)^2$$

Such modification of the parameters is in line with the method of least square, and its calculation is non-linear in the case of the present invention. When the above difference $\Delta$ is minimized, the function F with the parameters $a_1, a_2, \ldots a_m$ for the minimized difference $\Delta$ represents the desired refractive index profile of the cylinder being measured.

In the above approach of the least square method, the degree of approximation of the refractive index profile pattern depends on the number m of the parameters $a_1$ through $a_m$ of the function F. Depending on the purpose of the measurement of the refractive index profile, rough approximation or fine approximation may be selectively obtained by using suitable number of such parameters. The use of the method of least square is advantageous in that the influence of any error in the measurement of the individual incident positions and the individual true exit positions is minimized. The larger the number k of the rays entering the cylinder, the smaller the above influence of the measurement error will be.

The application of the method of measuring the refractive index profile of a cylinder according to the invention is not restricted to the measurement of such profile on a cross section perpendicular to the longitudinal axis of the cylinder, but the distribution of the refractive index in the longitudinal direction of the cylinder can be also measured by the method of the invention. To measure the longitudinal distribution, the cross section is shifted in steps in the longitudinal direction while taking the above cross-sectional measurement at each step.

Figure 3:
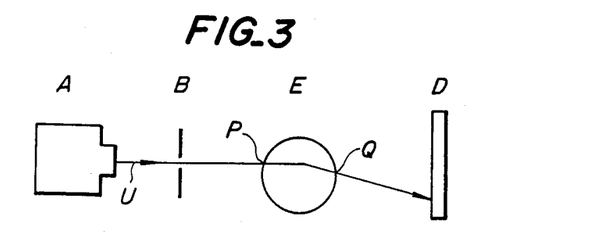
FIG. 3 is a schematic diagram illustrating essential elements of a device for practising the method according to the invention.

FIG. 3 shows an arrangement suitable for practising the method of the invention. The light from a light source A is sharply defined by a pinhole or slit B, and the sharply defined ray U is directed to a cylinder E at right angles to the longitudinal axis thereof so that the ray U becomes incident to the cylinder E at the incident position P. The incident ray U suffers from deflection while travelling through the cylinder E and leaves the cylinder E at a true exit position Q. A light sensor D spaced from the cylinder E determines the detected position where the ray U from the cylinder E arrives at the sensor D, and the true exit position Q on the peripheral surface of the cylinder E can be determined from the detected position of the ray. The relative position between the ray U and the cylinder E is shifted in steps, so as to obtain a series of data concerning the incident positions $P_i$ and the true exit positions $Q_i$.

Methods of measuring true exit positions will be explained.

(1) Method of measurement by varying a distance between the cylinder and the sensor.

Figure 3A:
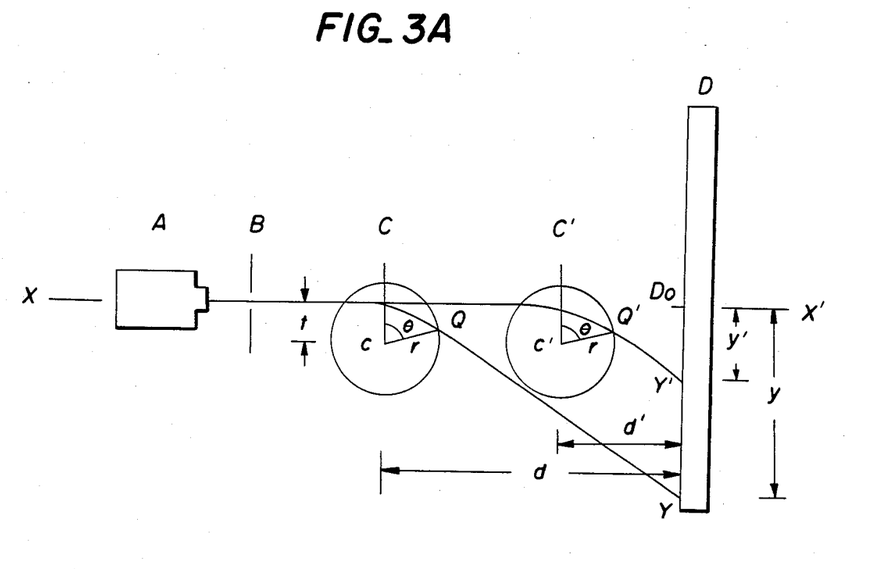
FIG. 3(a) and FIG. 3(b) are diagrammatic illustrations of the method of measuring the true exit positions by varying a distance between the cylinder and the sensor.

FIG. 3(a) is a schematic diagram showing the condition of the exit ray when the light ray exiting from the light source (A) is narrowly throttle by the pinhold or slit (B) and the incident in the cylinder (C, C') is caught by the sensor (D) which is placed perpendicularly to the optical axis X—X' of the light beam from the light source. The measurement is conducted by moving the cylinder in parallel to X—X' and varying a distance between the cylinder and the sensor. When the cylinder is at the position of C (center c), the light ray exits from the true exit position Q and reaches Y on the sensor. When the cylinder is at the position of C' (center c'), the light ray exits from the true exit position Q' and reaches Y' on the sensor. A distance t between X—X' and c or c' gives the incident position of the light ray. As the cylinder moves in parallel to X—X', the incident positions are naturally equal to each other at C and C'. The true exit position is given by an angle $\Phi$ specified in FIG. 2. Since the incident positions are equal to each other C and C', $\theta$ is also equal. Let the radius of the cylinder r, the distance from c and c' to the sensor D be d and d'. Distances y and y' from the center Do of the sensor to Y and Y' are obtained by measurement.

QY and Q'Y' are parallel to each other and the following equation is established.

$$\frac{d - r\sin\theta}{y - t + r\cos\theta} = \frac{d' - r\sin\theta}{y' - t + r\cos\theta} \tag{A-1}$$

Figure 3B:
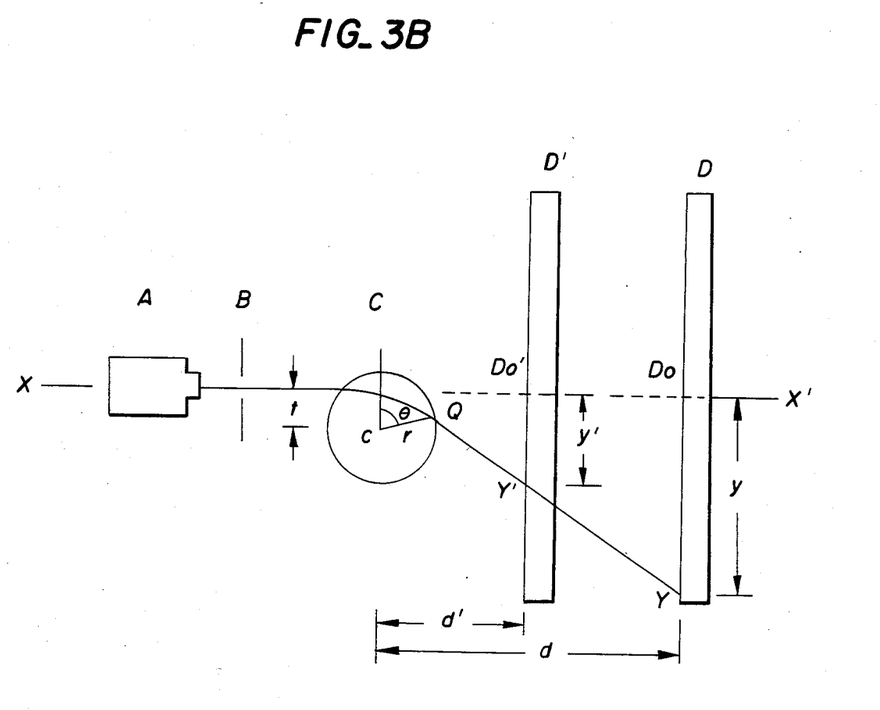

FIG. 3(b) is a schematic diagram showing the condition of the exit ray when the light ray exiting from the light souce (A) is narrowly throttled by the pinhole or slit (B) and the incident in the cylinder (C) is caught by the sensor (D, D') which is placed perpendicularly to the optical axis X—X' of the light beam from the light source. The measurement is conducted by moving the sensor in parallel to X—X' and moving a distance between the cylinder and the sensor. When the sensor is at the position of D (distance between the center c of the cylinder and the sensor is d ), the light ray exiting from the true exit position Q reaches Y on the sensor. When the sensor is at the position of D'(distance between the center c of the cyliner and the sensor is d'), the light ray exiting from the true exit position Q reaches Y' on the sensor. A distance t between X—X' and c gives the incident position of the light ray. The true exit position is given by an angle $\theta$ specified in FIG. 2. The radius r of the cylinder, the distance y from the center Do of the sensor to Y and the distance y' from the center Do' of the sensor to Y' are obtained by measurement.

Since the light ray after exiting goes straight, then Q, Y' and Y are on a straight line. Accordingly, the following equation is established.

$$\frac{d - r\sin\theta}{y - t + r\cos\theta} = \frac{d' - r\sin\theta}{y't + r\cos\theta} \tag{A-2}$$

The equations (A-1) and (A-2) are entirely the same. These equations are modified as follows.

$$(d - d')\cos\theta + (y - y')\sin\theta = \frac{d'y - dy' + dt - d't}{r} \tag{A-3}$$

The addition theorem of trigonometric function is applied as follows.

$$\sqrt{(d - d')^2 + (y \cdot y')^2} \, \cos(\theta - \alpha) = \frac{d'y - dy' + dt - d't}{r} \tag{A-4}$$

Except that $\alpha$ is an angle given by the following.

$$\cos\alpha = \frac{d - d'}{\sqrt{(d - d')^2 + (yy')^2}}, \tag{A-5}$$

$$\sin\alpha = \frac{y - y'}{\sqrt{(d - d')^2 + (yy')^2}}$$

and $\alpha = \tan^{-1}\frac{y - y'}{d - d'}$.

-continued $$\theta = \alpha + \cos^{-1} \frac{d'y - dy' + dt - d't}{r\sqrt{(d-d')^2 + (y-y')^2}}$$

And $\theta$ is obtained. The inverse of a trigonometric function can easily be calculated by a computer.

If the distance between the cylinder and the sensor is varied into two kinds as above, it is sufficient enough to obtain $\theta$, but if the distance between the cylinder and the sensor is changed variously, many measurements are carried out and the obtained values are averaged, it becomes possible to mitigate measurement error.

When the cylinder is once moved to the direction perpendicular to X—X' so as to change the incident position t and the methods of measurement described here are repeated, the true exit positions with respect to various incident positions can be obtained.

(2) Method for obtaining the true exit position with the use of a deflection angle $\Phi$.

Figure 3C:
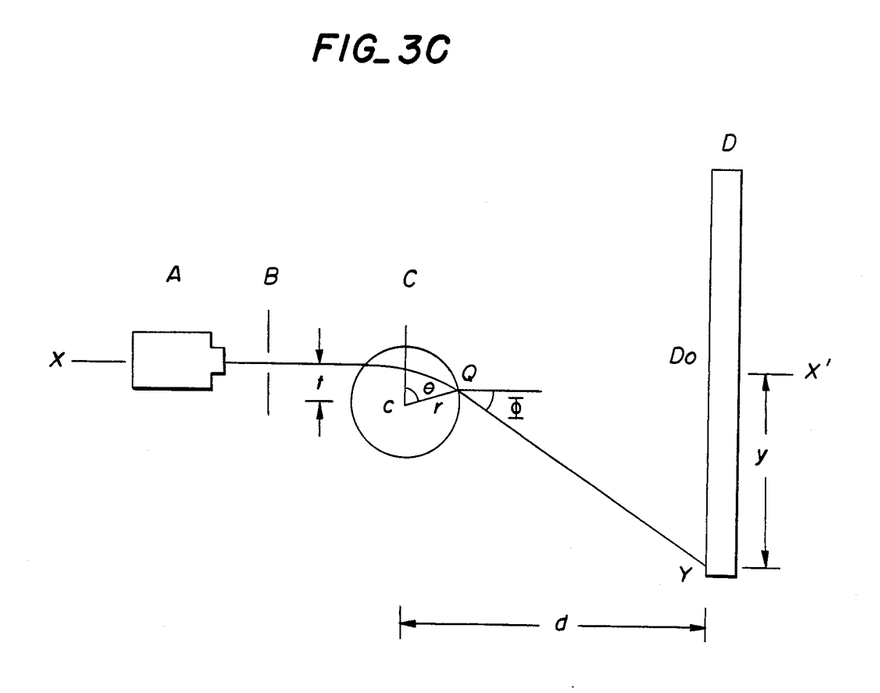
FIG. 3(c) is a diagrammatic illustration of the method for obtaining the true exit positions with the use of a deflection angle Φ.

FIG. 3(c) is a schematic diagram showing the condition of the exit ray when the light ray exiting from the light source (A) is narrowly throttle by the pinhole or slit (B) and the incident in the cylinder (C) is caught by the sensor (D) placed perpendicularly to the optical axis X—X' of the light beam from the light source. Let the center of the cylinder be c, a distance t between X—X' and c gives the incident position of the light ray. The light ray exists from the true exit position Q to the outside of the cylinder and reaches Y on the sensor. A distance from the center c of the cylinder to the sensor is d and a distance from the center Do of the sensor to X is y. As a method of measuring a deflection angle $\Phi$ of the exit light when t is at the incident position, a laser beam scanning method and a spatial filtering method have already been known, and $\Phi$ is supposed to be known by measurement with the use of either one of the above methods. The true exit position Q is given by a angle specified in FIG. 2. The radius of the cylinder is r.

A distance from Q to the sensor is given by $d - r \sin\theta$, and a distance from Q to X—X' is given by $t - r\cos\theta$. Accordingly, the following equation is established. As a modification, $$r \tan\Phi \sin\theta + r \cos\theta = \alpha \tan\Phi + t - y \quad \text{(A-7)}$$

Both sides are divided by r, $$\tan\Phi\sin\theta + \cos\theta = \frac{d\tan\Phi + t - y}{r} \quad \text{(A-8)}$$

From the definition of a trigonometric function, $\tan\Phi = \sin\Phi/\cos\Phi$, so that when both sides are multiplied by $\cos\Phi$, $$\sin\Phi\sin\theta + \cos\Phi\cos\theta = \frac{d\sin\Phi + (t-y)\cos\Phi}{r} \quad \text{(A-9)}$$

It is modified to the following by an addition theorem.

$$\cos(\theta - \Phi) = \frac{d\sin\Phi + (t-y)\cos\Phi}{r} \quad \text{(A-10)}$$

Accordingly, it becomes as follows.

$$\theta = \Phi + \cos^{-1}\left[\frac{d\sin\Phi + (t-y)\cos\Phi}{r}\right] \quad \text{(A-11)}$$

And $\theta$ is obtained. Calculation of the inverse of a trigonometric function can easily be carried out by a computer.

When the cylinder is moved to the direction perpendicular to X—X' so as to change the incident position t and the methods of measurement described here are repeated, the true exit positions with respect to various incident positions can be obtained.

An example of the derivation of mathematical equations representing the optical path in the cylinder E will be explained now.

Figure 5A:
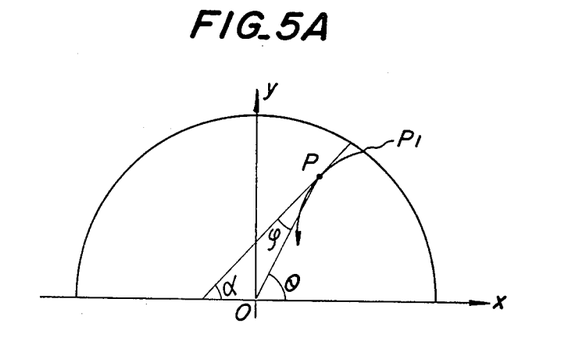
FIG. 5A FIG. 5B and FIG. 5C are diagrams which are used in deriving equations for calculating refractive index profiles.

Referring to FIG. 5A, it is assumed that the cylinder E has a refractive index n which is a function of only the distance r from the center O of the cross-section of the cylinder, i.e., $n=n(r)$. The orthogonal coordinates of the figure will be converted into polar coordinates, and a two-dimensional differential equation for the optical path will be derived. As to a line element ds along the optical path, there are the following relationships.

$$\frac{d}{ds}\left(n\frac{dx}{ds}\right) = \frac{x}{r}\frac{dn}{dr} \quad (1)$$

$$\frac{d}{ds}\left(n\frac{dy}{ds}\right) = \frac{y}{r}\frac{dn}{dr} \quad (2)$$

In view of the fact that $(1)y - (2)x = 0$ and an identity of $n(dx/ds)(dy/ds) - n(dy/ds)(dx/ds) = 0$, one can derive the following equation (3).

$$y\left(n\frac{dx}{ds}\right) - x\left(n\frac{dy}{ds}\right) = a \quad (3)$$

Here, a is a constant.

If the angle between the tangent to the optical path at an arbitrary point P of the optical path from the incident position $P_1$ and the x-axis is designated by $\alpha$ and the angle between the tangent and a line OP from the origin 0 to that point P is designated by $\Phi$, the two angles satisfy the following relations.

$$(nr) \sin\Phi = a \quad (4)$$

Geometrically, $$\sin\Phi = \frac{r}{\sqrt{r^2 + (dr/d\theta)^2}} \quad (5)$$

From the equations (4) and (5), the optical path in terms of its polar coordinate is given by $$\frac{dr}{d\theta} = \pm \frac{r}{a}\sqrt{n^2r^2 - a^2} \quad (6)$$

Figure 5B:
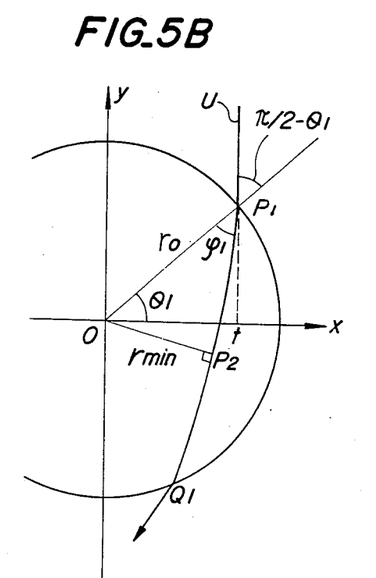

Referring to FIG. 5B, the cylinder may be treated as a lens having a certain refractive index profile, and the optical path of an incident ray which is parallel to and spaced by a distance t from the optical axis of the lens or the y-axis will be considered. If the radius of such lens is assumed to be $r_0$ and the refractive index of the medium surrounding the lens is assumed to be n, the above-mentioned constant a is given by $$a = \{n(r_0)\}r_0\sin(-\Phi_1) = -n_0 r_0 \sin\Phi_1 \quad (7)$$

here, $n_0 = n(r_0)$. By Snell's law, $$\frac{\sin\left(\frac{\pi}{2} - \theta_1\right)}{\sin\phi_1} = \frac{n_0}{n}, \quad \cos\theta_1 = t/r_0$$

Accordingly, $$\sin\phi_1 = \frac{n}{n_0}\sin\left(\frac{\pi}{2} - \theta_1\right) = \frac{n}{n_0}\cos\theta_1 = \frac{nt}{n_0 r_0} \quad (8)$$

From the equations (7) and (8), $$a = -n_0 r_0 \frac{nt}{n_0 r_0} = -nt$$

Substituting this relationship into the equation (6), $$\frac{dr}{d\theta} = \pm \frac{r}{nt}\sqrt{n^2 r^2 - n^2 t^2}$$

On the optical path of FIG. 5B, the point $P_2$ has a minimum distance to the center 0 of the orthogonal coordinates. In the optical path section between the incident position $P_1$ and the above position $P_2$ closest to the origin, the argument $\theta$ decreases with the decrease of the distance r from the origin. On the other hand, in the optical path section between the above position $P_2$ closest to the origin to the true exit position $Q_1$, the argument $\theta$ decreases with the increase of the distance r from the origin. Thus, the double sign in the last mentioned equation can be assigned as follows:

For the section from the incident position $P_1$ to the position $P_2$ closest to the origin, $$\frac{dr}{d\theta} = \frac{r}{nt}\sqrt{n^2 r^2 - n^2 t^2}$$

For the section from the position $P_2$ closest to the origin to the true exit position $Q_1$, $$\frac{dr}{d\theta} = -\frac{r}{nt}\sqrt{n^2 r^2 - n^2 t^2}$$

Figure 5C:
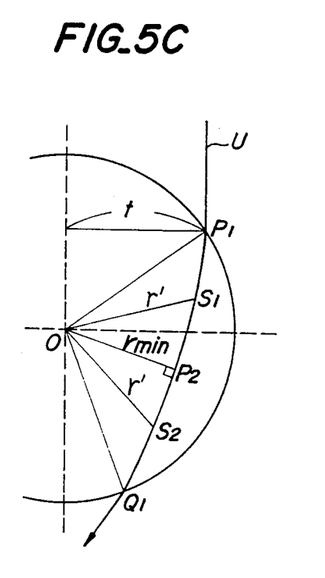

As can be seen from FIG. 5C, at the position $P_2$ closest to the origin, $r = r_{min}$ and $(dr/d\theta) = 0$, so that $$r_{min}/(nt) \times \sqrt{\{n(r_{min})\}^2 r_{min}^2 - n^2 t^2} = 0$$

Here, $n(r_{min})$ represents the refractive index at the position closest to the origin. Thus, the minimum distance to the origin $r_{min}$ can be given by $$r_{min} = (nt)/n(r_{min})$$

The inventors have succeeded in finding out the minimum distance $r_{min}$ by using the method of successive approximation based on the above equation.

Referring to FIG. 5C, the inventors confirmed by test that the distance r' from the origin 0 to that position $S_1$ or $S_2$ which lies on the optical path and has a refractive index n(r') could be determined by applying the method of successive approximation to the following equation.

$$r' = \frac{\sqrt{n^2 t^2 + nt\sqrt{n^2 t^2 + 4n^2(r')}}}{n(r')\sqrt{2}}$$

Thus, the following differential equations can be derived.

From position $P_1$ to position $S_1$, $\dfrac{d\theta}{dr} = \dfrac{nt}{r\sqrt{n^2 r^2 - n^2 t^2}}$ From position $S_1$ to position $P_2$, $\dfrac{dr}{d\theta} = \dfrac{r\sqrt{n^2 r^2 - n^2 t^2}}{nt}$ From position $P_2$ to position $S_2$, $\dfrac{dr}{d\theta} = -\dfrac{r\sqrt{n^2 r^2 - n^2 t^2}}{nt}$ From position $S_2$ to position $Q_1$, $\dfrac{d\theta}{dr} = -\dfrac{nt}{r\sqrt{n^2 r^2 - n^2 t^2}}$ The refractive index profile of a cylinder can be determined by numerically solving the above differential equations by the Runge-Kutta-Gill method. This approach to determining the refractive index can be also applied to lenses with distributed refractive index.

The invention will be described in further detail by referring to a numerical example.

EXAMPLE

Based on the actual data of a lens of distributed refractive index type, it was assumed that a glass cylinder with a radius $r_0 = 1$ mm had an "assumed refractive index profile" which profile was expressed by a function $n(r, n_0, g) = n_0\{1 - (gr)^2\}^{\frac{1}{2}}$, n being the refractive index, $n_0$ being the refractive index at the center of the cylinder and having a value of $n_0 = 1.602$, r being the distance from an arbitrary point in the glass cylinder to the center of the cylinder, and g being a focusing constant having a value of $g = 0.3000$ mm$^{-1}$.

The refractive index profile of the above glass cylinder was assumed to be measured by an arrangement as shown in FIG. 3 under the following conditions.

Distance from the sensor D to the center of the glass cylinder E: 15 mm

Fifteen parallel light rays U at an interval of 1/16 mm from one side of the glass cylinder E Three cases of environment: an index-matching fluid, water, and air The "measured value" in this Example was determined by calculation: namely, the optical path of each incident light ray U was calculated by numerical solution of the differential equations as described above, and the true exit position was determined from the optical path thus calculated, and then the position of the exit-side light ray U at the sensor D was calculated and assumed to be the measured value. Starting from the thus assumed measured value, the refractive index profile of the glass cylinder E was calculated in the following manner.

(1) The true exit positions $Q_i$ (i=1, 2, ..., 15) of the light rays from the glass cylinder E were calculated from the thus assumed measured value.

(2) Suitable initial values $n_0'$ and $g'$ for the refractive index at the center $n_0$ and the focusing constant $g$ of the refractive index profile equation $n(r, n_0, g)$ were assumed. See parenthesized values of Table 1.

(3) Phantom exit positions $Q_i'$ (i=1, 2, ..., 15) of the light rays from the glass cylinder were determined through calculation of the optical path based on the phantom refractive index profile equation $n=n_0'\{1-(g'r)^2\}^{\frac{1}{2}}$.

(4) The assumed initial values $n_0'$ and $g'$ for the refractive index at the center $n_0$ and the focusing constant $g$ were modified so as to minimize the sum of squared differences between the true exit positions $Q_i$ and the phantom exit positions $Q_i'$ by the method of least square.

(5) The phantom exit positions $Q_i'$ was revised by using the modified constants $n_0'$ and $g'$, and the modification of the preceding paragraph was repeated with the revised phantom exit positions $Q_i'$. Similar revision of the phantom exit positions $Q_i'$ and similar modification of the constants $n_0'$ and $g'$ were repeated until the values of the constants $n_0'$ and $g'$ converged. The converged values of the refractive index at the center $n_0'$ and the focusing constant $g'$ were assumed to represent the "measured refractive index profile" of the cylinder being measured.

Table 1 shows the assumed values of the refractive index at the center $n_0$ and the focusing constant $g$ for the "assumed refractive index profile" of the glass cylinder E for three cases: namely, the environments of an index-matching fluid, water and air. In the table, the parenthesized values are initial values assumed in the measurement. It was confirmed by tests that even when the initial values assumed in the measurement were quite different from the true values, satisfactory measurement was achieved.

When a glass cylinder has a large difference of refractive index between its peripheral portion and its environment, rays of light deflect considerably at the boundaries between the glass cylinder and the environment, and the contribution of the refractive index profile within the glass cylinder to the total deflection of ray will become small as compared with that of the glass-environment boundary. Accordingly, some difficulty was anticipated in measuring the refractive index profile under such conditions. However, the method of the invention uses only those constants $n_0$ and $g$ which are irrelevant to the environment medium surrounding the cylinder, and it has been proven by the numerical example that the measured profile is in excellent agreement with the assumed profile even when the environment has a different refractive index than that of the cylinder being measured.

Figure 4A:
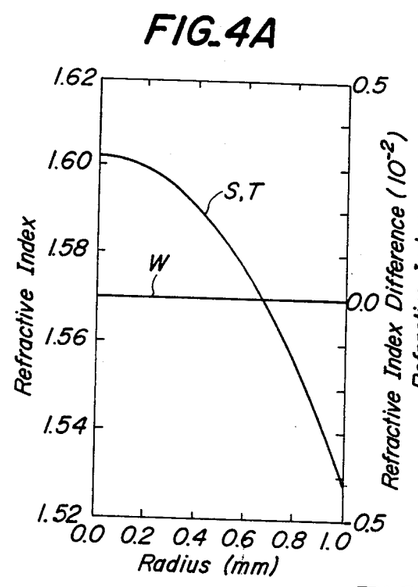
FIG. 4A, FIG. 4B and FIG. 4C are graphs showing the refractive index profiles of a cylinder placed in an index-matching fluid, water, and air respectively, which profiles are determined by calculation based on the method according to the present invention.
Figure 4B:
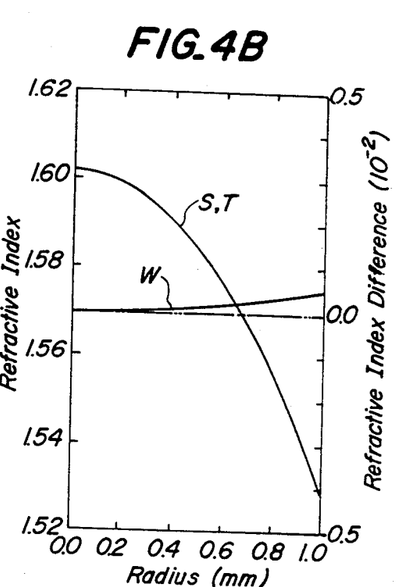
Figure 4C:
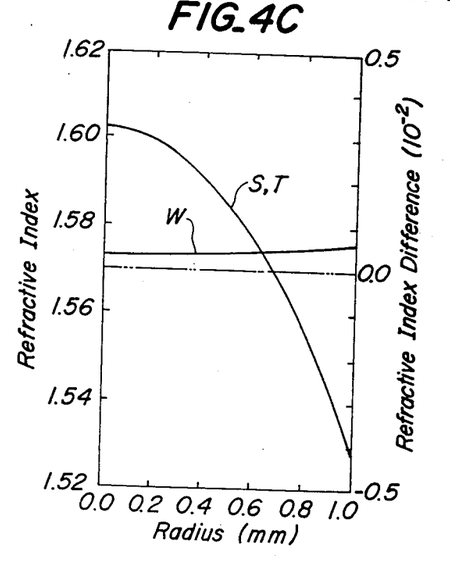

FIG. 4A, FIG. 4B and FIG. 4C show the results of the calculations for the glass cylinder in an index-matching fluid, water and air respectively. In the figures, the curves S show the assumed refractive index profile, while the curves T show the measured refractive index profile. The curves S and T are completely overlapped, so that the measured values are in excellent agreement with the assumed value. The curves W show the differences between the curves S and the curves T on the exaggerated scale. In short, the curves of the figures prove that the method of the invention provides excellent result.

TABLE 1

| Environment | $n_o$* | $g$** (mm$^{-1}$) |
|---|---|---|
| Assumed values | 1.602 | 0.3000 |
| Index-matching fluid | 1.602 | 0.3000 |
|  | (1.623) | (0.3160) |
| Water | 1.602 | 0.2992 |
|  | (1.627) | (0.2939) |
| Air | 1.602 | 0.2992 |
|  | (1.644) | (0.2504) |

*refractive index at the center of cylinder
**focusing constant

As described in the foregoing, the method of measuring the refractive index profile of a cylinder according to the invention measures not the deflection angle but the true exit position, so that measurement is not affected by the environment and the following effects can be achieved.

(a) The refractive index profile of a cylinder can be measured without being influenced by the refractive index of the medium surrounding the cylinder, so that restrictions on the measuring environment are substantially eliminated. Thus, the method of the invention can be used at any stage of the production of cylindrical optical elements, and it is very useful in the process control and quality control of cylindrical optical elements.

(b) The method of the invention can be applied not only to the refractive index profile measurement of a preform for the production of optical fibers, but also to the measurement of the internal refractive index profile of a lens of distributed refractive index type having a large difference of refractive index between its central and peripheral portions.

(c) Influence of the measurement error is minimized because the measured data are processed by the method of least mean square.

(d) The degree of approximation can be easily selected by choosing proper number of parameters in the function representing the refractive index profile. Thus, either detailed or rough approximation can be used depending on the need of specific application.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. A method of measuring refractive index profile of a cylinder, comprising steps of:

applying k distinct parallel rays of light to the cylinder so that the rays enter the cylinder at incident positions $P_1, P_2, \ldots, P_k$ and leave the cylinder at true exit positions $Q_1, Q_2, \ldots, Q_k$, said rays being on one plane perpendicular to longitudinal axis of said cylinder;

measuring said true exit positions;

assuming a mathematical function representing a phantom refractive index profile of the cylinder on said plane;

calculating phantom exit positions $Q_1', Q_2', \ldots, Q_k'$ for the parallel rays from said incident positions based on said assumed mathematical functions;

modifying said mathematical function so as to minimize a sum of the squared distances between the true and phantom exit positions for the rays from said incident positons, wherein said mathematical function is in the form of $$F(r, a_1, a_2, \ldots, a_m),$$

r being distance from an arbitrary point to the longitudinal axis f of the cylinder, $a_1$ through $a_m$ being parameters representing pattern of the refractive index profile of the cylinder, the number m of the parameters being not greater the number k of the rays ($k \geq m$), whereby the thus modified function represents the refractive index profile of the cylinder.

2. A method of measuring refractive index profile of a cylinder, comprising steps of:

applying k distinct parallel rays of light to the cylinder so that the rays enter the cylinder at incident positions $P_1, P_2, \ldots, P_k$ and leave the cylinder at true exit positions $Q_1, Q_2, \ldots, Q_k$, said rays being on one plane perpendicular to longitudinal axis of said cylinder;

measuring said true exit positions;

assuming a mathematical function representing a phantom refractive index profile of the cylinder on said plane;

calculating phantom exit positions $Q_1', Q_2', \ldots, Q_k'$ for the parallel rays from said incident positions based on said assumed mathematical function;

modifying said assumed mathematical function so as to minimize a sum of the squared distances between the true and phantom exit positions for the rays from said incident positions, wherein said mathematical function is in a form of $$n(r, n_0, g) = n_0\sqrt{1-(gr)^2},$$

n being refractive index, $n_0$ being refractive index at the longitudinal axis of the cylinder, r being distance from an arbitrary point in the cylinder to said longitudinal axis of the cylinder, and g being a focusing constant, whereby the thus modified mathematical function represents the refractive index profile of the cylinder.

3. A method of measuring refractive index profile of a cylinder, comprising steps of:

applying k distinct parallel rays of light to the cylinder so that the rays enter the cylinder at incident positions $P_1, P_2, \ldots, P_k$ and leave the cylinder at true exit positions $Q_1, Q_2, \ldots, Q_k$, said rays being on one plane perpendicular to longitudinal axis of said cylinder;

measuring said true exit positions;

assuming a mathematical function representing a phantom refractive index profile of the cylinder on said plane;

calculating phantom exit positions $Q_1', Q_2', \ldots, Q_k'$ for the parallel rays from said incident positions based on said assumed mathematical function;

modifying said mathematical function so as to minimize sum of squared distances between the true and phantom exit positions for the rays from said incident positions;

shifting said plane in the longitudinal direction of the cylinder while keeping the plane perpendicular to said longitudinal axis; and, determining a refractive index profile on the thus moved plane, whereby the thus modified mathematical function represents the refractive index profile of the cylinder and the refractive index profile in the longitudinal direction of the cylinder is measured.

4. A method of measuring refractive index profile of a cylinder, comprising steps of:

applying k distinct parallel rays of light to the cylinder so that the rays enter the cylinder at incident positions $P_1, P_2, \ldots, P_k$ and leave the cylinder at true exit positions $Q_1, Q_2, \ldots, Q_k$, said rays being on one plane perpendicular to longitudinal axis of said cylinder measuring said true exit positions;

assuming a mathematical function representing a phantom refractive index profile of the cylinder on said plane;

calculating phantom exit positions $Q_1', Q_2', \ldots, Q_k'$ for the parallel rays from said incident positions based on said assumed mathematical function;

modifying said mathematical function so as to minimize sum of squared distances between the true and phantom exit positions for the rays from said incident positions;

shifting said plane in the longitudinal direction of the cylinder while keeping the plane perpendicular to said longitudinal axis; and, determining a refractive index profile on the thus moved plane, wherein said mathematical function is in a form of $$F(r, a_1, a_2, \ldots, a_m),$$

r being distance from an arbitrary point to the longitudinal axis of the cylinder, $a_1$ through $a_m$ being parameters representing pattern of the refractive index profile of the cylinder, the number m of the parameters being not greater the number k of the rays ($k \geq m$), whereby the thus modified function represents the refractive index profile of the cylinder, and the refractive index profile in the longitudinal direction of the cylinder is measured.

5. A method of measuring refractive index profile of a cylinder, comprising steps of:

applying k distinct parallel rays of light to the cylinder so that the rays enter the cylinder at incident positions $P_1, P_2, \ldots, P_k$ and leave the cylinder at true exit positions $Q_1, Q_2, \ldots, Q_k$, said rays being on one plane perpendicular to longitudinal axis of said cylinder;

measuring said true exit positions;

assuming a mathematical function representing a phantom refractive index profile of the cylinder on said plane;

calculating phantom exit positions $Q_1', Q_2', \ldots, Q_k'$ for the parallel rays from said incident positions based on said assumed mathematical function;

modifying said mathematical function so as to minimize sum of squared distances between the true and phantom exit positions for the rays from said incident positions;

shifting said plane in the longitudinal direction of the cylinder while keeping the plane perpendicular to said longitudinal axis; and, determining a refractive index profile on the thus moved plane, wherein said mathematical function is in a form of $$n(r, n_0, g) = n_0\sqrt{1-(gr)^2},$$

n being refractive index, $n_0$ being refractive index at the longitudinal axis of the cylinder, r being distance from an arbitrary point in the cylinder to said longitudinal axis of the cylinder, and g being a focussing constant, whereby the thus modified function represents the refractive index profile of the cylinder and the refractive index profile in the longitudinal direction of the cylinder is measured.

* * * * *